(12) United States Patent
Criscione

(10) Patent No.: US 8,679,512 B2
(45) Date of Patent: Mar. 25, 2014

(54) TOPICAL FORMULATION COMPRISING A CORTICOSTEROID AS ACTIVE INGREDIENT

(75) Inventor: Salvatore Criscione, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/462,245

(22) Filed: May 2, 2012

(65) Prior Publication Data

US 2012/0301511 A1 Nov. 29, 2012

(30) Foreign Application Priority Data

May 4, 2011 (EP) .................................. 11164815

(51) Int. Cl.
- *A61K 9/12* (2006.01)
- *A61K 9/14* (2006.01)
- *A61K 9/16* (2006.01)
- *C07J 5/00* (2006.01)

(52) U.S. Cl.
USPC ............... 424/400; 424/45; 424/46; 424/493; 514/828; 514/861; 514/863; 514/887; 552/574

(58) Field of Classification Search
None
See application file for complete search history.

(56) References Cited

U.S. PATENT DOCUMENTS

| | | | |
|---|---|---|---|
| 5,158,761 A | 10/1992 | Kamishita et al. | |
| 6,780,398 B1 * | 8/2004 | Akutsu et al. | 424/45 |

FOREIGN PATENT DOCUMENTS

| | | |
|---|---|---|
| DE | 43 16 727 | 11/1994 |
| WO | 2011/026076 | 3/2011 |

OTHER PUBLICATIONS

Google search string for "anhydrous dextrose"; downloaded Feb. 28, 2013.*
Google search string for "topical vs. nasal administration forms"; downloaded Feb. 28, 2013.*
Oino Food Ltd. specification for Dextrose Anhydrous; provided 2001; last updated Apr. 20, 2004; downloaded Feb. 28, 2013.*
Definition for "nasal decongestant" from TheFreeDictionary.com (http://medical-dictionary.thefreedictionary.com/Topical+decongestant), downloaded Feb. 28, 2013.*
European Search Report in Application No. 11164815.0, issued Oct. 6, 2011.

* cited by examiner

*Primary Examiner* — Robert A Wax
*Assistant Examiner* — Jeffrey T Palenik
(74) *Attorney, Agent, or Firm* — Oblon, Spivak, McClelland, Maier & Neustadt, L.L.P.

(57) ABSTRACT

Topically administering a propellant-free formulation as a spray in the form of aqueous suspension of drug particles,
  wherein said formulation consists essentially of:
    micronized particles of beclometasone dipropionate (BDP) suspended in an aqueous phase,
    said aqueous phase comprising:
    an emulsifying agent selected from the class of polysorbates in an amount of 0.1 to 0.2% w/v, based on the total volume of the formulation;
    a sugar or a sugar alcohol in an amount of 5.0 to 5.2% w/v, based on the total volume of the formulation;
    a mixture of microcrystalline cellulose and carboxymethylcellulose sodium in an amount of 0.5 to 1.0% w/v, based on the total volume of the formulation;
    one or more preservatives; and
    water up to 100%,
  is effective for the prophylaxis and/or treatment of a dermatological disease such as atopic dermatitis, acne and psoriasis.

16 Claims, No Drawings

TOPICAL FORMULATION COMPRISING A CORTICOSTEROID AS ACTIVE INGREDIENT

CROSS REFERENCES TO RELATED APPLICATIONS

This application claims priority to European Patent Application No. 11164815.0, filed on May 4, 2011, which is incorporated herein by reference in its entirety.

BACKGROUND OF THE INVENTION

1. Field of the Invention

The present invention relates to formulations in form of an aqueous suspension of drug particles of a corticosteroid. The present invention also relate to the use of such a formulation for topical administration for the prophylaxis and/or treatment of a dermatological disease such as atopic dermatitis, acne and psoriasis. The present invention also relates to processes for preparing such a formulation and methods of administering such a formulation onto the skin, in the form of a spray.

2. Discussion of the Background

In humans, the skin is the largest organ of the integumentary system, i.e. system that protects the body from damage. It is made of three main layers, i.e.: i) the epidermis which is the most superficial layer of skin, and is principally constituted of keratinocyte cells; ii) the dermis, which is the intermediate layer constituted of collage, elastic fibers, and extrafibrillar matrix; and iii) the subcutaneous tissue which is a deep layer of fat underlying the fascia.

There are many conditions or diseases that could affect the skin collectively known as dermatitis or dermatoses. Dermatitis symptoms vary with all different forms of the condition. They range from skin rashes to bumpy rashes or including blisters.

The prevention or treatment of disease states or conditions of the skin has traditionally used simple local delivery systems. In particular, topical corticosteroids, such as bethametasone 17-valerate, bethametasone dipropionate, and beclometasone dipropionate, are widely used as active ingredients primarily because of their anti-inflammatory, antipruritic, and vasoconstrictive actions.

Current corticosteroid-containing products are available mainly as aerosol foams, creams, gels, lotions, shampoos, or ointments that are supplied in tubes or bottles and applied to an affected area of the skin by hand (finger tips).

Many formulations such as creams, lotions, or ointments are greasy, and hence are unpleasant to apply on large areas of the skin. Moreover, the ineffectiveness of said formulations is also observed, since they are generally too viscous to allow efficient penetration of the active agent in the epidermis. In addition, some conventional cream and ointment bases are irritating to the skin, particularly over the long exposure that is frequently required for efficacy, and the fluidity of lotions often makes the physical application difficult to control over a desired area. Moreover, it is necessary to rub such formulations into the target site to improve the penetration of the active agent into the epidermis, an action which itself produces irritation. Furthermore, sensitization by the formulation components to environmental agents (e.g. U.V. rays) has always to be taken into account.

The formulations in form of pressurized aerosol (propellant based) formulations often contain ethanol and hence they suffer of the well known adverse effects of ethanol, i.e., irritation. Additionally, said formulations have the disadvantage of relatively high cost, primarily due to the construction of the containers and metering valves. Other formulations contain other irritant vehicles or solvents such as propylene glycol, and hence such formulations do not promote patient compliance.

Several formulations are also available that cause substantial foam formation upon spraying onto the skin, which is highly undesirable to a patient using such preparations for aesthetic reasons.

Moreover, it should be highlighted that in many skin diseases the process of keratinization is disturbed resulting in an increased transepidermal water loss. A consequence of this can be poor skin structure leading to bacterial infection, penetration of allergens or toxic materials as well as increased water loss further exacerbating the disease.

To overcome this problem, an occlusive barrier constituted of a plastic film is often applied to the skin during application to enhance the retention of the moisture. A commonly used film is composed of a polyvinylidene chloride (PVDC) copolymer. This way of occluding the surface of the skin, however, is difficult to administer and contraindicated in certain skin diseases such as psoriasis.

Alternatively, moisturizing agents are sometimes added, but some of these excipients may be irritants and not well-tolerated so much as that some of the relevant formulation may also contain soothing agents that prevent irritation such as aloe, green tea, chamomile, licorice root, or allantoin.

A further disadvantage of conventional formulations is that their active agents act for a short duration of time and do not efficaciously reach the deeper derma stratum but only penetrate into the superficial epidermis.

They thus require frequent re-application, thereby providing a negative impact on treatment compliance and quality of life of the patient, with often a enhancement of drop out due to the lack of compliance.

Furthermore, the presence of high levels of corticosteroids in the superficial epidermis may cause undesired effects such as thinning of the skin (atrophy), which sometimes results in unaesthetic permanent stretch marks (striae).

In summary, the disadvantages of topical corticosteroid-based formulations vary, in that they can often irritate normal skin, be time consuming and awkward to apply, cannot be used for long periods, can stain clothing, and/or have an objectionable odor.

As a result, it is sometimes difficult for people to maintain regular applications of these medications.

On the other hand, sudden withdrawal of corticosteroids can cause an aggressive recurrence of the condition. This is known as "rebound" of the condition.

Topical formulations free of some of the aforementioned disadvantages are disclosed in WO 2011/026076, which is incorporated herein by reference in its entirety. However, its teaching is substantially directed to the preparation of oil-in-water emulsion wherein the corticosteroid, being hydrophobic, would be dissolved in the oil phase, making it more prone for absorption.

In addition, to favor the penetration of the active ingredient in the derma and hence its efficacy, in the formulations of WO 2011/026076, significant amounts of surfactant agents and penetration enhancers are added. Both of these features could contribute to significantly increase the penetration of the active agent not only into the derma but also in the subcutaneous tissue, which in turn could give rise to an increased absorption into the bloodstream.

On the other hand, it is known that the side-effects of corticosteroids mainly occur at the systemic level, and that children in particular, are at a higher risk of systemic side effects. Such effects are dose dependent at topical as well as systemic levels. It means that, as a general therapeutical agreement, the optimal dosing schedule is that which, with the minimum dosage, still provides efficacy (mostly relief of symptoms).

Moreover, it is known that a high amount of certain surfactant agents could be irritating due to their capacity of sequestering lipids, that are important components of the hydrophobic water-protective barrier of the skin.

There remains, therefore, an unmet need for improved patient compliant topical formulations that are effective in the treatment of skin disorders.

SUMMARY OF THE INVENTION

Accordingly, it is one object of the present invention to provide novel formulations for topical administration for use for the prevention and/or treatment of a skin disease.

It is another object of the present invention to provide novel formulations for topical administration for use for the prevention and/or treatment of a skin disease, which are well tolerated.

It is another object of the present invention to provide novel formulations for topical administration for use for the prevention and/or treatment of a skin disease, which have a high level moisturizing activity.

It is another object of the present invention to provide novel formulations for topical administration for use for the prevention and/or treatment of a skin disease, which are characterized by an efficacious penetration of therapeutic agent into the derma without any significant systemic absorption.

It is another object of the present invention to provide novel processes for preparing such a formulation.

It is another object of the present invention to provide novel devices which contain such a formulation.

It is another object of the present invention to provide novel methods for the prophylaxis and/or treatment of a dermatological disease such as atopic dermatitis, acne and psoriasis by topically administering such a formulation.

These and other objects, which will become apparent during the following detailed description, have been achieved by the inventors' discovery that propellant-free pharmaceutical formulations for topical administration, comprising micronized particles of beclometasone dipropionate (BDP) as active ingredient suspended in an aqueous phase, said aqueous phase consisting of an emulsifying agent selected from the class of polysorbates in an amount of 0.1 to 0.3% w/v, a sugar or a sugar alcohol as tonicity agent in an amount of 5.0 to 5.2% w/v, a mixture of microcrystalline cellulose and carboxymethylcellulose sodium as a thickening agent in an amount of 0.5 to 1.0% w/v, one or more preservatives, and water up to 100%, are effective for the prophylaxis and/or treatment of dermatological diseases.

Thus, in a first aspect, the present invention provides propellant-free pharmaceutical formulations for topical administration, comprising micronized particles of beclometasone dipropionate (BDP) as active ingredient suspended in an aqueous phase for use for the prophylaxis and/or treatment of a dermatological disease, said aqueous phase consisting of an emulsifying agent selected from the class of polysorbates in an amount of 0.1 to 0.3% w/v, a sugar or a sugar alcohol as tonicity agent in an amount of 5.0 to 5.2% w/v, a mixture of microcrystalline cellulose and carboxymethylcellulose sodium as a thickening agent in an amount of 0.5 to 1.0% w/v, one or more preservatives, and water up to 100%.

In a second embodiment, the present invention provides a formulation herein described filled in a device for its topical delivery in the form of a spray.

In a third embodiment, the present invention provides the use of the aforementioned formulation in the manufacture of a medicament for the prophylaxis and/or treatment of skin diseases.

In a fourth embodiment, the present invention provides methods of preventing and/or treating skin diseases, which comprise topical administration to a patient of an effective amount of the aforementioned formulation.

In a fifth embodiment, the present invention provides process for preparing such a formulation.

In a sixth embodiment, the present invention provides process for preparing such a device.

DETAILED DESCRIPTION OF THE PREFERRED EMBODIMENTS

The terms "active drug," "active ingredient," "active," "active substance," "active compound," and "therapeutic agent" are used synonymously.

The term "corticosteroids" refers to class of active ingredients having a hydrogenated cyclopentoperhydrophenanthrene ring system endowed with an anti-inflammatory activity.

The term "beclometasone dipropionate" refers to the chemical compound (8S,9R,10S,11S,13S,14S,16S,17R)-9-chloro-11-hydroxy-10,13,16-trimethyl-3-oxo-17-[2-(propionyloxy)acetyl]-6,7,8,9,10,11,12,13,14,15,16,17-dodecahydro-3H-cyclopenta[a]phenanthren-17-yl propionate.

The term "propellant free" indicates that the formulation is not delivered in admixture with any of the commonly used aerosol propellants, such as hydrofluorocarbons, hydrocarbons, compressed gases, and the like.

The term "spray" means to disperse the formulation as a mass or jet of droplets from a suitable dispensing device.

"Therapeutically effective dose" refers to the quantity of active ingredient administered at one time by spraying upon each single actuation (shot) of the device.

The term "preservative" refers to any natural or synthetic chemical substance added to prevent decomposition by microbial growth or by undesirable chemical changes.

In the present application, the particle size is quantified by measuring a characteristic equivalent sphere diameter, known as volume diameter by laser diffraction. The volume diameter (VD) is related to the mass diameter (MD) by the density of the particles (assuming a size independent density for the particles). Particle size distribution is usually described by: i) the volume median diameter (VMD) which corresponds to the diameter of 50 percent by volume of the particles [d(v, 0.5)], and ii) the VD (MD) in micron of 10% and 90% of the particles [d(v,0.1) and d(v,0.9)].

The term "chemically stable" refers to stability of the active agent in the formulation, wherein changes in the drug assay values and/or impurities content are less than about 10%, preferably less than 5%, during storage at 25° C. and 60% relative humidity (RH), or 40° C. and 75% RH, for durations such as 3, 6, 12, 18, or 24 months.

In the context of the suspension formulations, the expression "physically stable" refers to formulations which exhibit substantially no growth in particle size or change in crystal morphology of the active ingredient over a prolonged period, are readily redispersible, and upon redispersion, do not flocculate so quickly as to prevent reproducing dosing of the active ingredient.

The term "dermatological disease" includes conditions or diseases that could affect the skin collectively known as dermatitis or dermatoses.

The term "prophylaxis" means an approach for reducing the risk of onset of a disease or a fastidious condition.

The term "treatment" means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

According to the present invention, the propellant-free pharmaceutical formulation is utilized for topical administration and is actuated by delivering a therapeutically effective dose as a spray directly onto the affected part of the skin.

The active ingredient is beclometasone dipropionate that is present as micronized particles suspended in an aqueous phase. Said corticosteroid turned out to be very well tolerated by the skin.

Preferably, the beclometasone dipropionate (BDP) is crystalline and may be present in its anhydrous form or in its monohydrated form.

In a particular embodiment, crystalline BDP is present as the anhydrous form, while in another particular embodiment, BDP is present as the monohydrated form.

Inter alia, the two forms are commonly distinguished by their powder X-ray diffractometry pattern.

Advantageously, at least 99% of the suspended particles of the active ingredient have a volume diameter equal to or less than 20 microns, at least 90% of said particles [d(v,0.9)] have a volume diameter equal to or lower than 10 microns, and at least 50% of said particles [d(v,0.5)] have a volume diameter equal to or less than 6 microns, preferably less than 5 microns.

The particle size of the active substance is determined by measuring the characteristic equivalent sphere diameter, known as volume diameter, by laser diffraction, preferably using a Malvern apparatus available from Malvern Instruments Ltd.

The active ingredient is advantageously present in an amount of 0.01 to 0.1% w/v, advantageously 0.015 to 0.080% w/v, based on the total volume of the formulation, so as to deliver a therapeutically effective dose of beclometasone dipropionate of 25 to 100 μg per actuation. The amount is preferably 0.0385 to 0.077% w/v.

In another embodiment, the therapeutically effective dose might be 50 to 100 μg per actuation, 25 to 50 μg per actuation.

In a preferred embodiment, the therapeutically effective dose might be 50 μg per actuation, while in another preferred embodiment might be 100 μg per actuation.

In a further embodiment, the dose may be of 25 μg per actuation.

The formulation is free of ethanol, propylene glycol and of any other irritating solvents. It is also free of soothing agents commonly used to prevent irritation such as aloe, green tea, chamomile, licorice root or allantoin.

The aqueous phase of the formulation consists of water, preferably purified water, in which are dissolved or suspended:

i) an emulsifying agent selected from the class of polysorbates, in an amount of 0.1 to 0.3% w/v, preferably 0.1 to 0.2% w/v, more preferably in an amount of 0.1% w/v, based on the total volume of the formulation.

Polysorbates are a class of non-ionic emulsifiers, commercially available under the trademark of Tween™ or Span™, that derive from PEGylated sorbitan esterified with fatty acids. Advantageously, said agent is polysorbate 20 or polysorbate 80. In a preferred embodiment, said agent is polysorbate 20.

ii) a sugar or a sugar alcohol, as a tonicity agent, in an amount of 5.0 to 5.2% w/v, preferably of 5.1 w/v, based on the total volume of the formulation. Advantageously, the tonicity agent is selected from the group consisting of glucose monohydrate, mannitol, sorbitol, and xylitol, and preferably is glucose monohydrate, also known in the Pharmacopoeias as dextrose.

iii) a mixture of microcrystalline cellulose and carboxymethylcellulose sodium as a thickening agent in an amount of 0.5 to 1.0%, preferably of 0.8% w/v, based on the total volume of the formulation.

and iv) one or more preservatives.

The mixture of microcrystalline cellulose and carboxymethylcellulose sodium is a commercial item, available under the trademark of AVICEL® RC/CL.

The preservatives are advantageously present in an amount of 0.25 to 0.30% w/v, preferably 0.27 to 0.29% w/v, based on the total volume of the formulation.

Said preservative is preferably phenylethyl alcohol or benzalkonium chloride or a mixture thereof, in a ratio comprised of 95:5 to 85:15, preferably of 90:10.

The formulation herein described exhibits a homogenous distribution of the particles as well as a high level of chemical and physical stability.

Since it is in form of suspended particles in the formulation, the active ingredient is slowly absorbed from the skin, and hence its duration of action is prolonged, thereby reducing the number of applications required.

It has also been found that, upon spraying and evaporation of the water, the mixture of microcrystalline cellulose and carboxymethylcellulose sodium in the specific amount used together with the tonicity agent form a thin film on the skin favoring the retention of moisture, and hence hydration, so soothing the risk of skin drying and irritation.

Said film is not greasy and hence is well tolerated by the patient.

Moreover, it has been found that the emulsifying agent in the specific claimed amount used herein partially acts as a soft penetration enhancer favoring the absorption into the derma, so reducing the levels of the drug into the epidermis, to which atrophy of the skin might be associated as reported above. Considering that the target for pharmacological activity is the dermis, this is expected to give a better therapeutic effect.

On the other hand, the subcutaneous absorption is also reduced as compared to formulations wherein harder penetration enhancers are present, thereby reducing the risks of the systemic side-effects.

Without being limited by the theory, it may be hypothesized that the optimized absorption property of the formulation herein described may also be due to the formation of the thin film.

The formulation may be prepared according to known processes.

Typically, the process of preparation comprises the following steps:

(a) an aqueous solution comprising the suitable excipients is prepared in a suitable tank, then transferred to a turboemulsifier provided with a turbine adapted for homogenizing the suspension, and optionally with a mechanical agitator;

(b) the active ingredient in the form of a micronized particles is added to the aqueous solution;

(c) the suspended particles of the active ingredient are homogenized by stirring; and (d) optionally the resulting suspension is submitted to a further step of homogenization in a high-pressure homogenizer;

Advantageously, the process is performed according to the conditions described in WO 00/25746, which is incorporated herein by reference in its entirety.

Preferably, the active ingredient is loaded into the turboemulsifier under vacuum according to the conditions described in WO 03/086374, which is incorporated herein by reference in its entirety.

The micronization step may be carried out according to known procedures, for example by grinding using a conventional fluid energy mill such as the jet mill apparatus.

The formulation herein described may also comprise one or more additional active ingredients suspended or dissolved in the aqueous phase.

Further active ingredients that could advantageously be used are those useful for the treatment of dermatological diseases such as tretinoin and immunosuppressive agents.

The topical formulations herein described may be applied directly onto affected areas of the skin as a spray. The strength of the formulation and hence the dose of the steroid to be applied will depend on the severity of the disease, the age of the patient, and the extent of the affected area.

For children, it would be preferable to use a formulation capable of delivering a therapeutically effective dose of BDP of 25 or 50 µg per actuation, while for adults, it would be more advantageous to use a formulation capable of delivering 50 or 100 µg per actuation.

Typically, the disease shall be treated by delivering from one to six shots of the formulation, depending on the extent of the affected area, till disappearance of the signs of the disease.

The administration could be carried out once or twice daily, preferably twice daily, typically by keeping the spray at a distance of about 20 cm from the skin to optimally cover the desired area with one shot.

Further aspects of the present invention also provide dispensing devices for the topical delivery of the formulation onto the skin in the form of sprays. In certain embodiments, the present invention provides devices, into which the formulation is filled, comprising a container, a dispenser and a closure. The closures used for packaging could be made of a polymeric substance such as high-density polyethylene (HDPE), low-density polyethylene (LDPE), or resins. The closures are particularly in the form of caps that are fitted onto the containers to aid in providing support to the dispenser unit and/or to shield the contents of the container from the outside environment. Various container materials include, but are not limited to, tin plated steel, aluminum, stainless steel, plastics, and glass.

An example of a dispenser is a unit containing a pump that can be adapted to fit on any type of container, such as by threads that match threading on the container. The pump is capable of dispensing the sprayable formulations described herein through a dip tube extending into a container from an actuator and attached to a one-way valve, which releases the formulation from an orifice in the actuator in the form of a spray.

The valve may be a metering valve. Various types of valves that can be used include, but are not limited to, continuous spray valves and metering valves. The actuators allow for easy opening and closing of the valve and are an integral part of a package. Various types of actuators include but are not limited to spray actuators, foam actuators, solid-stream actuators, and special actuators. In another embodiment, a dispensing device may be a device comprising a container, having therein a pouch system or bag containing the product, optionally fitted with a dip tube and an actuator fitted with a valve wherein the container is filled with nitrogen gas or compressed air, surrounding the pouch or bag. Containers can be made of aluminum or tin plate and the pouch system or bag containing the product can be made of layers of polyethylene (PE), polypropylene (PP), polyethylene terephthalate (PET), and aluminum.

The pouch can have a dip tube therein, communicating with the actuator valve, to control the spray rate and reduce droplet size. In other embodiments, a dispensing device useful for dispensing the formulations herein described provides spray rates and spray patterns, in a manner such that substantially uniform dosage is dispensed each time which appreciably covers the desired affected area of the skin onto which the formulation is sprayed.

Devices frequently provide a reproducible distribution of droplets, in distributions where about 90% of the droplets have sizes ranging from about 1 to about 500 microns. The orifice is sized to control the droplet sizes of the dispensed product. The orifice size also affects the provision of a uniform characteristic spray pattern.

The formulations herein described can be applied in an essentially easier and more exact way than creams and ointments can be applied, since for the spray application it is only necessary to spray a given volume, whereas the application of the semi-solid products requires an easily accessible and visual estimation of the cream amount or the ointment amount. Further, smearing and soiling of clothing can more easily be avoided on large surface areas.

For the spray compositions, spreading and rubbing are not necessarily required, contrary to cream and ointment products, since the layer formed on the body surface by evaporation or vaporization of the liquid already has an ideal fine dispersion of active agent; hence "pressure pain" will not occur from the topical application of spray formulations herein described.

Administration of the formulation herein described may be indicated for the prophylaxis and/or treatment of a wide range of dermatological diseases or conditions including, but not limited to, contact dermatitis, atopic dermatitis, seborrheic dermatitis, autosensitization dermatitis, stasis dermatitis, asteatotic eczema, nummular eczema, psoriasis, rosacea, peri-oral dermatitis, scabies, leg ulcers, tuberculous, ringworm or viral skin disease, discoid lupus erythematosus, various forms of lichen such as lichen planus and lichen sclerosus. Moreover, it could be conveniently utilized for the treatment of different forms of erythema, in particular sun erythema, insect bites or stings, post allergic tests, phimosis and anal/perianal inflammation.

Preferably said formulation is utilized for the treatment of atopic dermatitis, eczema, and psoriasis.

Other features of the invention will become apparent in the course of the following descriptions of exemplary embodiments which are given for illustration of the invention and are not intended to be limiting thereof.

EXAMPLES

Example 1

Suspension Formulations Comprising BDP 50 and 100 µg

The formulations were prepared starting from micronized anhydrous beclometasone dipropionate (BDP) according to the preparation process disclosed in WO 00/25746, which is incorporated herein by reference in its entirety. In particular, two formulations capable of delivering 50 μg and 100 μg per actuation were prepared. Their compositions (mg/100 ml) are reported in Tables 1 and 2.

TABLE 1

Formulation 50 μg per actuation.

| Ingredients | Quantity (mg/100 ml) |
|---|---|
| Micronized BDP | 38.5 |
| Polysorbate 20 | 100.0 |
| Microcrystalline cellulose and Carboxymethylcellulose sodium | 800.0 |
| Glucose monohydrate | 5100.0 |
| Benzalkonium chloride | 27.0 |
| Phenylethyl alcohol | 255.0 |
| Purified water | q.s. for 100 ml |

TABLE 2

Formulation 100 μg per actuation.

| Ingredients | Quantity (mg/100 ml) |
|---|---|
| Micronizd BDP | 77.0 |
| Polysorbate 20 | 100.0 |
| Microcrystalline cellulose and Carboxymethylcellulose sodium | 800.0 |
| Glucose monohydrate | 5100.0 |
| Benzalkonium chloride | 27.0 |
| Phenylethyl alcohol | 255.0 |
| Purified water | q.s. for 100 ml |

Both the suspension formulations are physically stable and show a good homogeneity of the active ingredient.

Example 2

Suspension Formulation Comprising BDP 25 μg

A formulation capable of delivering 25 μg per actuation is prepared starting from micronized anhydrous beclometasone dipropionate (BDP). Its composition (mg/100 ml) is reported in Table 3.

TABLE 3

Formulation 25 μg per actuation.

| Ingredients | Quantity (mg/100 ml) |
|---|---|
| Micronized BDP | 19.25 |
| Polysorbate 80 | 100.0 |
| Microcrystalline cellulose and Carboxymethylcellulose sodium | 800.0 |
| Glucose monohydrate | 5100.0 |
| Benzalkonium chloride | 27.0 |
| Phenylethyl alcohol | 255.0 |
| Purified water | q.s. for 100 ml |

Comparative Example 3

Formulation According to WO 2011/026076 (Example 2G)

The formulation, which in form of emulsion, has the following composition:

TABLE 4

| Ingredients | Quantity (% v/v) |
|---|---|
| Beclomethasone dipropionate | 0.077 |
| PEG-6 palmitostearate ethylene glycol palmitostearate PEG-32 palmitostearate | 7.500 |
| Mineral oil | 7.060 |
| Oleoyl polyoxylglycerides | 2.940 |
| Diethyleneglycol monoethyl ether | 10.000 |
| Propylparaben | 0.800 |
| Methylparaben | 0.200 |
| Butylated hydroxytoluene | 0.050 |
| Hydroxyethyl cellulose | 0.100 |
| Water | 71.273 |

Preparation Process:
a) Polyethylene glycol and ethylene glycol palmitostearate, oleoyl polyoxyglycerides and mineral oil are mixed and heated to about 50° C.
b) Propylparaben, methylparaben and butylated hydroxytoluene are mixed with the liquid a) with continuous stirring at about 50° C.
c) Beclomethasone dipropionate is mixed with diethyleneglycol monoethyl ether.
d) Material of c) is mixed with material of b).
e) Hydroxyethyl cellulose is dissolved in water.
f) The aqueous phase of e) is slowly added to the oily phase of d) at about 50° C. with continuous stirring.
g) The mixture of f) is homogenized and allowed to cool to ambient temperature.

Comparative Example 4

Formulation According to U.S. Pat. No. 5,158,761 (Example 5)

The formulation, which in form of suspension, has the following composition.

TABLE 5

| Ingredients | Quantity (% v/v): |
|---|---|
| Beclomethasone dipropionate | 0.10 |
| Polysorbate 80 | 0.01 |
| Glycerin | 1.00 |
| Carbopol 934 (4% aqueous solution) | 15.00 |
| Sodium hydroxide (2% aqueous solution) | 10.00 |
| Sodium chloride (10% aqueous solution) | 8.00 |
| Purified water | 65.89 |

Preparation Process:
a) A 2% aqueous solution of sodium hydroxide is added to a 4% aqueous solution of carbopol 934 gradually with stirring, and mixture is stirred until it became gel.
b) A suspension of beclomethasone dipropionate in polysorbate 80, glycerin and purified water is gradually added to mixture a) and it is stirred uniformly.
c) The viscosity of the mixture is adjusted with 10% aqueous solution of sodium chloride and the mixture is stirred uniformly.

Example 5

Skin Permeation Testing

The aim of this study was to evaluate the permeation and skin retention (in the epidermis and in the dermis) of beclomethasone dipropionate (BDP) from the formulation 100 μg per actuation of Example 1 in comparison with the formulations of the prior art prepared according to example 5 of U.S. Pat. No. 5,158,761 and example 2G of WO 2011/026076, both of which are incorporated herein by reference in their entireties. A skin permeation study is conducted using skin samples according to the test procedure described below.

Full thickness pig ear skin samples, obtained from a local slaughterhouse, are used. The samples are stocked at −20° C. for not longer than 3 months.

$$Q_x(\mu g) = C_e * V_e$$

where:
$C_e$=active concentration in the extraction solution (μg/ml)
$V_e$=volume of extraction solution (ml)
The amount of active recovered per mg of tissue (Q) is calculated as:

$$Q(\mu g/mg) = Q_x/W$$

where W represents the weight of the tissue (mg).
The results are reported in Table 6.

TABLE 6

Skin recovery (data expressed as absolute amount of BDP recovered in the tissues).

Formulation 100 μg per actuation of Example 1

| Amount Applied (μL) | Application time (h) | Epidermis recovery (μg) | SD | RSD % | Dermis recovery (μg) | SD | RSD % | replicates |
|---|---|---|---|---|---|---|---|---|
| 10 | 4 | 1.98 | 0.60 | 30.15 | 0.71 | 0.10 | 14.60 | 4 |
| 10 | 8 | 1.28 | 0.53 | 41.06 | 1.12 | 0.58 | 51.58 | 8 |

| Applied quantity (μL) | Application time (h) | Epidermis recovery (μg) | SD | RSD % | Dermis recovery (μg) | SD | RSD % | replicates |
|---|---|---|---|---|---|---|---|---|
| Formulation according to WO 2011/026076 | | | | | | | | |
| 10 | 4 | 0.30 | 0.09 | 29.00 | 0.15 | 0.04 | 28.41 | 7 |
| 10 | 8 | 0.23 | 0.12 | 52.93 | 0.13 | 0.06 | 43.93 | 6 |
| Formulation according to U.S. Pat. No. 5,158,761 | | | | | | | | |
| 10 | 4 | 3.41 | 1.82 | 53.41 | 0.38 | 0.28 | 74.04 | 14 |
| 10 | 8 | 2.67 | 1.99 | 74.40 | 0.59 | 0.25 | 42.63 | 14 |

The samples are thawed at room temperature just before use and cleaned from the subcutaneous fat using a scalpel. The average thickness of the skin samples is recorded.

The experiments are performed in Franz-type diffusion cells. The surface area of each cell is 0.6 cm².

Skin samples, approximately 1.5×1.5 cm, are mounted with the corneal side facing the donor chamber. The receptor chamber contains about 4 ml of saline solution (NaCl 0.9% with 2.5% of 2-hydroxypropyl-β-cyclodextrin) termostatted at 37° C. and magnetically stirred. A variable volume (5 μl, 10 μl, 15 μl) of formulations is applied on the corneal side facing, in the donor chamber.

At the predetermined time intervals, 300 μl of receptor solution is withdrawn from the receptor compartment for analysis. After sampling, the same volume of fresh solution will be added to the receptor solution.

At the end of the in vitro experiments (typically 4 or 8 hours), the cell is dismantled, the receptor formulation remove by aspiration and the skin washed, by using isopropanol. The skin is then punch biopsied (0.6 cm²). The epidermis is peeled off with forceps, after heating for 20 seconds with hot air. After separation, epidermis and dermis are introduced in pre-weighted Eppendorf tubes and weighted.

From each sample of epidermis and dermis, the active is extracted using 1 ml of the appropriate solvent:
Extraction solvent: $CH_3CN:CH_3OH:H_2O$ (19.5:45.5:35 v/v/v)
Conditions: 1 ml of solvent, overnight at room temperature.
After extraction, the solutions are mixed, filtered, and analyzed by HPLC. BDP and its main metabolites, 17-BMP and 21-BMP, were determined.

The amount of active recovered in the dermis and epidermis samples ($Q_x$) is calculated as:

The conclusions of the study are the following:
BDP was never found in the receptor compartment for all formulations tested.
No metabolites of BDP were found in any of the samples, suggesting that hydrolysis is not a big issue in the topical application of BDP.
The application time (4 vs 8 hours) and amount of formulation applied do not seem to influence the amount of BDP recovered.

However, from the results reported in Table 6, it can be appreciated that the formulation of Example 1 results in lower amounts accumulated in the epidermis and higher amounts in the dermis than the two comparative formulations (at 4 and 8 hours of application time).

Considering that the target for pharmacological activity is the dermis, the formulation of Example 1 is expected to give a better therapeutic effect compared to formulations of the prior art.

Moreover the formulation according to example 5 of U.S. Pat. No. 5,158,761 is an emulsion with poor physical stability (it tends to separate into the two phases within a few minutes from preparation) and this can be the cause of the very high variability (that made it necessary to increase the number of replicates to 12).

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for the treatment of a dermatological disease, comprising topically administering an effective amount of a propellant-free pharmaceutical formulation as a spray to a subject in need thereof,
wherein said formulation consists of:
micronized particles of beclometasone dipropionate (BDP) suspended in an aqueous phase,
said aqueous phase comprising:
an emulsifying agent selected from the class of polysorbates in an amount of 0.1 to 0.2% w/v, based on the total volume of the formulation;
a sugar or a sugar alcohol in an amount of 5.0 to 5.2% w/v, based on the total volume of the formulation;
a mixture of microcrystalline cellulose and carboxymethylcellulose sodium in an amount of 0.5 to 1.0% w/v, based on the total volume of the formulation;
one or more preservatives; and
water up to 100%,
wherein said dermatological disease is atopic dermatitis, acne, or psoriasis, and
wherein said formulation is administered in such an amount that said beclometasone dipropionate is administered in an amount of 25 to 100 µg.

2. A method according to claim 1, wherein said beclometasone dipropionate is present in said formulation in its anhydrous form.

3. A method according to claim 1, wherein said beclometasone dipropionate is present in said formulation in its monohydrate form.

4. A method according to claim 1, wherein said beclometasone dipropionate is present in said formulation in an amount of 0.01 to 0.1% w/v, based on the total volume of the formulation.

5. A method according to claim 4, wherein said beclometasone dipropionate is present in said formulation in an amount of 0.015 to 0.080% w/v, based on the total volume of the formulation.

6. A method according to claim 5, wherein said beclometasone dipropionate is present in said formulation in an amount of 0.0385 to 0.077% w/v, based on the total volume of the formulation.

7. A method according to claim 1, wherein said emulsifying agent is polysorbate 20 or polysorbate 80.

8. A method according to claim 1, wherein sugar or sugar alcohol is present in said formulation in an amount of 5.1% w/v, based on the total volume of the formulation.

9. A method according to claim 8, wherein said sugar or sugar alcohol is selected from the group consisting of glucose monohydrate, mannitol, sorbitol, xylitol, and a mixture thereof.

10. A method according to claim 9, wherein said sugar or sugar alcohol is glucose monohydrate.

11. A method according to claim 1, wherein said mixture of microcrystalline cellulose and carboxymethylcellulose sodium is present in said formulation in an amount of 0.8% w/v, based on the total volume of the formulation.

12. A method according to claim 1, wherein said said one or more preservatives is present in said formulation in an amount of 0.25 to 0.30% w/v, based on the total volume of the formulation.

13. A method according to claim 12, wherein said said one or more preservatives is phenylethyl alcohol or benzalkonium chloride or a mixture thereof.

14. A method according to claim 1, wherein said formulation is administered from a device for topical delivery in the form of a spray.

15. A method according to claim 1, wherein said formulation is administered in such an amount that said beclometasone dipropionate is administered in an amount of 50 to 100 µg.

16. A method according to claim 1, wherein said formulation is administered in such an amount that said beclometasone dipropionate is administered in an amount of 25 to 50 µg.

* * * * *